United States Patent [19]
Grassi et al.

[11] Patent Number: 5,078,701
[45] Date of Patent: Jan. 7, 1992

[54] WIRE GUIDED INTESTINAL CATHETER

[75] Inventors: Clement J. Grassi, Watertown, Mass.; Richard L. Nelson, Jr., Wilmette, Ill.

[73] Assignee: Bissell Medical Products, Inc., Naperville, Ill.

[21] Appl. No.: 593,051

[22] Filed: Oct. 5, 1990

[51] Int. Cl.$^5$ ............................................. A61M 5/00
[52] U.S. Cl. ..................................... 604/264; 604/280; 604/270; 604/54
[58] Field of Search ............... 604/270, 280, 281, 282, 604/283, 264, 54, 275

[56] References Cited

U.S. PATENT DOCUMENTS

| | | |
|---|---|---|
| 2,857,915 | 10/1958 | Sheridan . |
| 4,027,659 | 7/1977 | Slingluff . |
| 4,182,787 | 1/1980 | Goossens et al. ............... 428/36 |
| 4,270,542 | 6/1981 | Plumley ............................ 604/270 |
| 4,368,739 | 1/1983 | Nelson, Jr. ....................... 604/54 |
| 4,451,257 | 6/1984 | Atchley ............................ 604/119 |
| 4,613,323 | 9/1986 | Norton et al. .................... 604/54 X |
| 4,642,092 | 2/1987 | Moss ................................ 604/280 X |
| 4,676,778 | 6/1987 | Nelson, Jr. ....................... 604/45 |
| 4,704,111 | 11/1987 | Moss ................................ 604/280 X |
| 4,781,704 | 11/1988 | Potter .............................. 604/270 |
| 4,828,550 | 5/1989 | Kurimoto ........................ 604/270 X |
| 4,838,879 | 6/1989 | Tanabe et al. ................... 604/280 |
| 4,874,365 | 10/1989 | Frederick et al. ............... 604/54 |

OTHER PUBLICATIONS

"Modified Gastrojejunostomy Tube: Percutaneous Placement for Gastric Decompression and Jejunal Feeding", Grassi, Clement J., *Radiology*, Dec. 1989, vol. 173, pp. 875-876.

*Primary Examiner*—John D. Yasko
*Attorney, Agent, or Firm*—Marshall, O'Toole, Gerstein, Murray & Bicknell

[57] ABSTRACT

An intestinal catheter is inserted into the gastrointestinal tract by use of a guide wire and performs the functions of aspirating the stomach and feeding the small intestine. A feeding lumen communicates with an opening in the downstream end of the catheter. The guide wire can be inserted in the feeding lumen of the catheter when emplacing the catheter into a patient's gastrointestinal tract.

22 Claims, 3 Drawing Sheets

FIG. 7
FIG. 8
FIG. 9
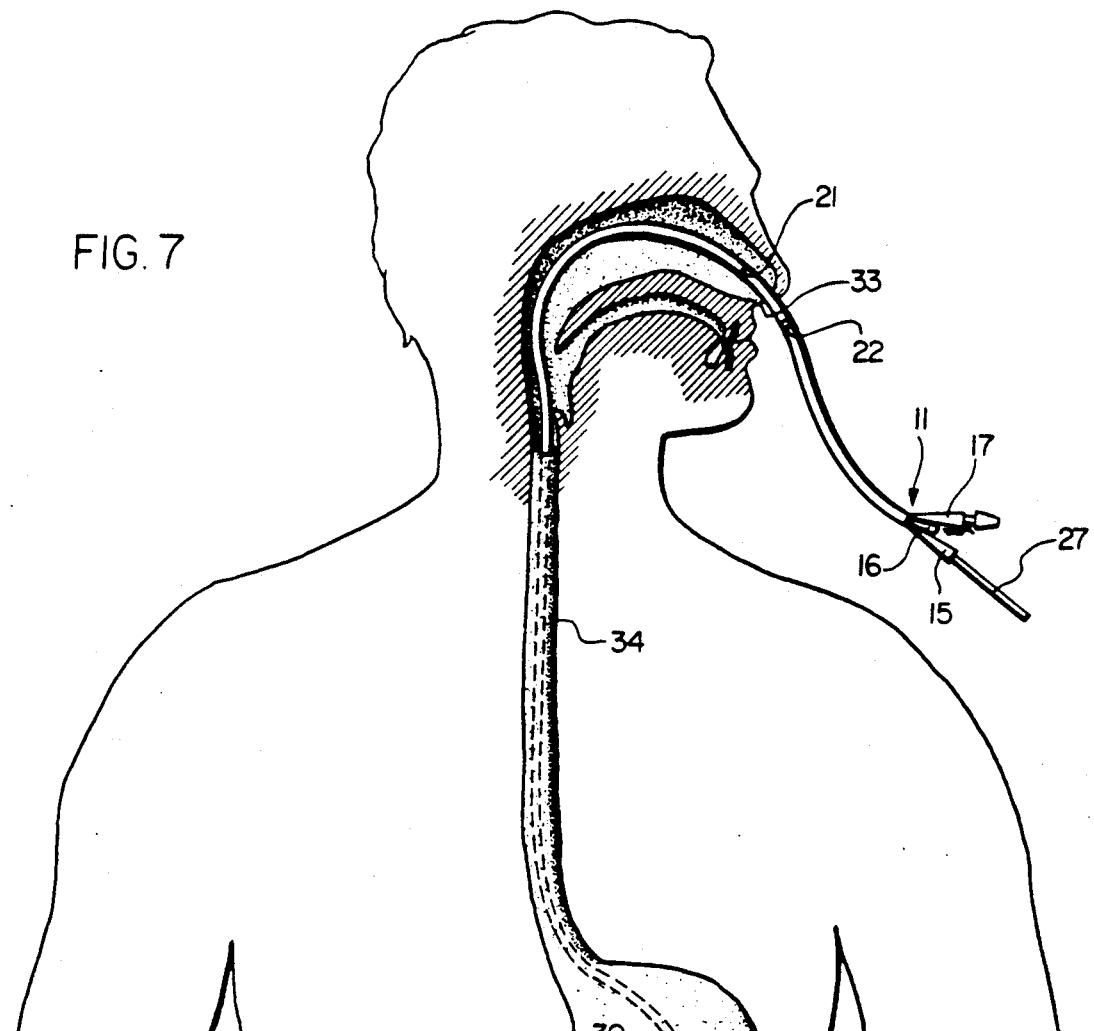
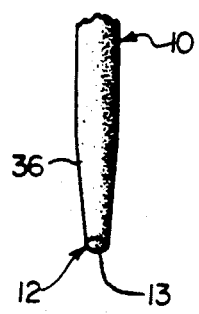
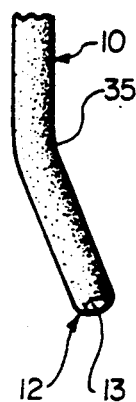

WIRE GUIDED INTESTINAL CATHETER

BACKGROUND OF THE INVENTION

The present invention relates generally to intestinal catheters and more particularly to an intestinal catheter, inserted by use of a guide wire, for aspirating the stomach and feeding the small intestine.

The gastrointestinal tract comprises, in descending order from the mouth or nose, the esophagus, the stomach, the small intestine and the large intestine. The small intestine or bowel comprises, in descending order, the duodenum, connected to the stomach through an opening called the pylorus, the jejunum, which connects with the duodenum at a location identified by an adjacent ligament called the Ligament of Treitz, and the illium, which in turn connects with the large bowel.

It is often desirable to emplace within the gastrointestinal tract a catheter where the downstream end of the catheter is located in the small intestine. Nelson, U.S. Pat. No. 4,676,778 and Nelson, U.S. Pat. No. 4,368,739 describe devices which can be emplaced within the small intestine. Those devices are designed to be inserted during surgery and are provided with pairs of inflatable balloons which facilitate the manipulation of the catheter through the small intestine. Because those devices require manual manipulation of the intestinal tract, they are inserted only during surgery.

There are techniques for insertion of intestinal catheters which do not involve surgery. Single lumen feeding tubes have been inserted into the intestine by use of a guide wire. The guide wire is inserted into the tube, and the pair are inserted into the gastrointestinal tract. The catheter and guide wire are moved through the gastrointestinal tract by manipulating the guide wire at the upstream or operator end of the tube. A radiologist uses a flouroscope to determine the position of the guide wire and catheter and to aid in moving them further through the gastrointestinal tract.

When a catheter is emplaced in the gastrointestinal tract, it may be necessary to replace the catheter periodically or to insert a catheter which can perform functions different than the originally emplaced catheter. For instance, if there has been emplaced a catheter that supplies nutritive material to the stomach, it may be desirable to remove that catheter and replace it with one which aspirates the stomach and supplies nutritive material to the intestine. It may also be desirable to emplace the new catheter without surgery and, thus, without the use of inflatable balloons to aid in moving the catheter through the gastrointestinal tract.

SUMMARY OF THE INVENTION

There is provided in accordance with the present invention a single tube or catheter which performs the dual functions of aspirating the stomach and feeding liquid into the small intestine for nourishing the patient. The catheter can be inserted nasally or by a gastrostomy, a procedure where an opening is made through a patient's skin into the stomach. A gastrostomy can be accomplished surgically by making an incision or percutaneously by inserting a sharp pointed object, such as a needle or stylet, through the skin and into the stomach.

The catheter of the present invention can be emplaced by use of a guide wire and can easily replace a previously emplaced catheter.

The catheter comprises a flexible tube having upstream and downstream ends. The tube has three lumens: a first lumen for feeding, a second lumen for suction and a third lumen which serves to vent the suction lumen. Near the upstream end of the tube is a fitting for connecting the suction lumen to suction, a fitting for connecting the feeding lumen to a source of nutritive or medicinal material and structure for venting the vent lumen to atmosphere.

The tip of the downstream end of the tube has an opening. The tip opening is connected to the feeding lumen and allows feeding material to exit the tube and flow into the small intestine.

A plurality of gastric openings are located in the wall of the tube near the middle of the catheter. These gastric openings are connected to the suction lumen and allow material to be aspirated from the stomach.

A channel connects the vent lumen with the suction lumen. The channel is located downstream of the most downstream of the suction openings. The channel allows air to enter the suction lumen to aid in unclogging the suction lumen when the stomach is being aspirated.

The tube has a radio-opaque stripe along its entire length, and the downstream end of the tube is coated with a radio-opaque material. These radio-opaque features can be viewed by a radiologist through a flouroscope to determine whether the catheter has been properly emplaced within the gastrointestinal tract.

The tube is emplaced within the gastrointestinal tract by use of a guide wire. In one procedure, the guide wire can be inserted all the way into a previously emplaced catheter and held in place in the gastrointestinal tract while the previously emplaced catheter is removed over the guide wire. The upstream end of the emplaced guide wire remains outside of the patient's body, and this end is then inserted through the tip opening of a fresh, unemplaced catheter and into the feeding lumen. The catheter is then advanced over the guide wire until the downstream end of the catheter reaches the tip of the guide wire. The catheter can be inserted further into the gastrointestinal tract by viewing the guide wire and catheter through a flouroscope and manipulating the upstream end of the guide wire.

In another procedure, where no catheter has been previously emplaced, the catheter can be inserted into the patient in the first instance by emplacing a guide wire in the feeding lumen and then introducing the guide wire and catheter together into the patient's body while viewing them through a flouroscope and manipulating the guide wire's upstream end.

Other features and advantages are inherent in the catheter claimed and disclosed or will become apparent to those skilled in the art from the following detailed description in conjunction with the accompanying diagramatic drawings.

BRIEF DESCRIPTION OF THE DRAWINGS

FIG. 7 is a diagrammatic view of the human body showing a catheter constructed in accordance with the present invention emplaced within the gastrointestinal tract through the nose.

FIGS. 8 and 9 are fragmentary side views of a portion of a catheter constructed in accordance with the present invention.

DETAILED DESCRIPTION

Figure 1:
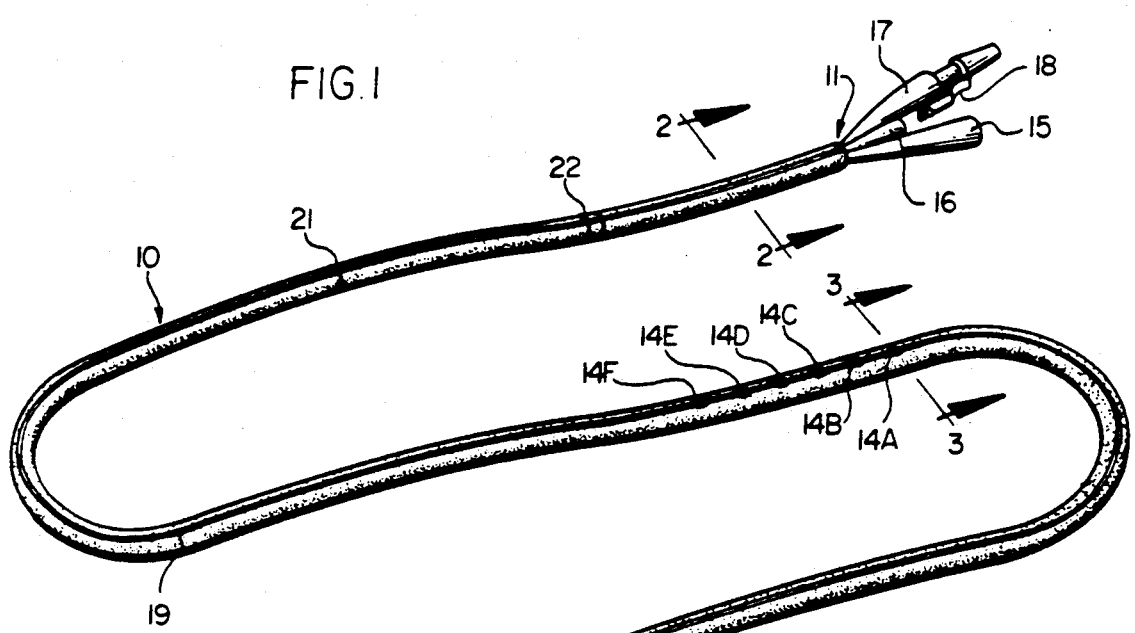
FIG. 1 is a perspective of an embodiment of a catheter constructed in accordance with the present invention.
Figure 2:
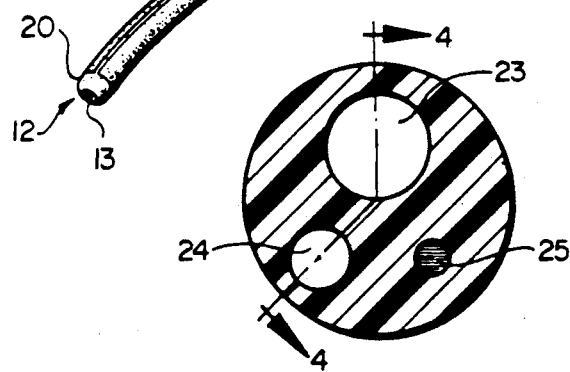
FIG. 2 is a sectional view taken along line 2—2 in FIG. 1.

Referring initially to FIG. 1, there is illustrated a catheter constructed in accordance with an embodiment of the present invention and comprising a flexible tube indicated generally at 10 having an upstream end indicated generally at 11 and a downstream end indicated generally at 12. The tube may be made out of any suitable material including polyurethane or polyvinyl chloride.

Located within tube 10 (FIGS. 2-5) is a suction lumen 23, a feeding lumen 24 and a vent lumen 25.

Figure 4:
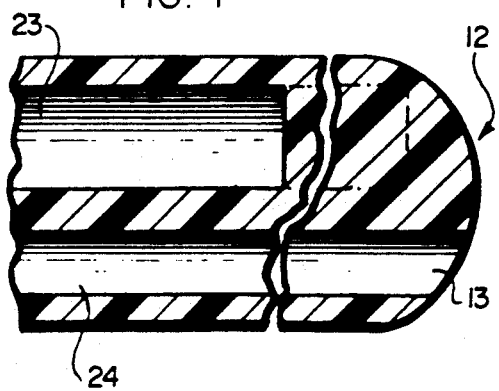
FIG. 4 is a sectional view taken along line 4—4 in FIG. 2.

At the tube's downstream end 12 is a tip opening 13 communicating with feeding lumen 24 (FIG. 4). At upstream end 11 is a fitting 15 for connecting feeding lumen 24 to a source of nutritive or medicinal material (FIG. 1). When the catheter is emplaced within the gastrointestinal tract, feeding material enters fitting 15 and passes through feeding lumen 24 to tip opening 13 from where it enters the small intestine. Additional openings (not depicted) may be placed near downstream end 12, communicating with feeding lumen 24, in order to provide additional avenues for feeding material to enter the small intestine.

Figure 3:
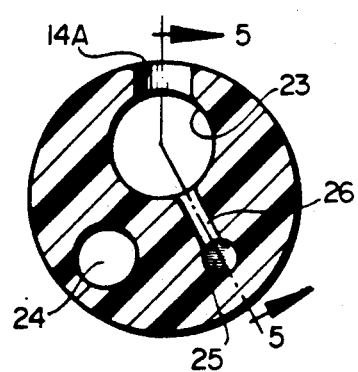
FIG. 3 is a sectional view taken along line 3—3 in FIG. 1.
Figure 5:
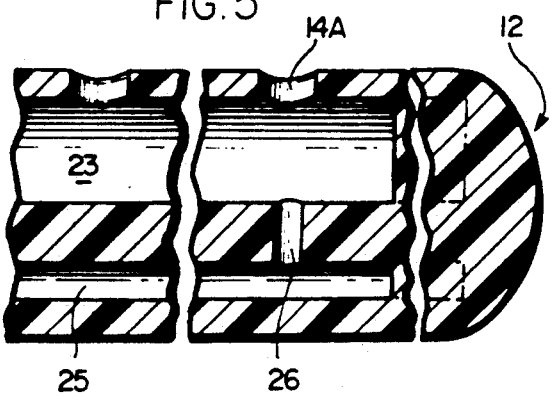
FIG. 5 is a sectional view taken along line 5—5 in FIG. 3.

Near the middle of tube 10 are gastric openings 14A-14F. Each gastric opening 14A-14F communicates with suction lumen 23 (FIGS. 3 and 5). The tube has a length such that when downstream end 12 is in the small intestine, at least some of gastric openings 14A-14F are in the stomach.

At the upstream end of the tube is a suction connection fitting 17 (FIG. 1), for connecting suction lumen 23 to a suction source, and a suction control element 18.

Vent lumen 25 is connected to suction lumen 23 by a vent channel 26 (FIGS. 3 and 5). Vent channel 26 is located at or downstream of the furthest downstream of the gastric openings 14A-14F. In the embodiment of the invention depicted in FIGS. 1-5, channel 26 is adjacent to gastric opening 14A. At the tube's upstream end 11 is a vent fitting 16 for connecting vent lumen 25 with the atmosphere (FIG. 1). Channel 26, vent lumen 25 and vent fitting 16 together comprise structure for preventing plugging of gastric openings 14A-14F by the lining of the stomach when the stomach is being aspirated. Absent some preventive expedient, the stomach lining can be sucked up against gastric openings 14A-14F and plug them. Because catheter 10 includes channel 26, vent lumen 25 and vent fitting 16, continuous suction can be employed through lumen 23 without manually interrupting the suction or without employing a complicated automatic suction interrupting valve, and there will be no plugging of gastric openings 14A-14F by the lining of the stomach.

Suction lumen 23 and vent lumen 25 serve no purpose downstream of vent channel 26. Therefore, in the embodiment of the invention depicted, those lumens have been plugged or terminate just downstream of vent channel 26 (FIG. 5).

The catheter depicted in FIG. 1 has a radio-opaque stripe 19 on the exterior surface of the tube, running from downstream end 12 to upstream end 11. Radio-opaque stripe 19 is comprised of a material which can be viewed through a flouroscope when the catheter has been emplaced in the patient's body. Gastric openings 14A-14F are located on an area of the exterior surface of tube 10 in line with radio-opaque stripe 19. When viewed under a flouroscope, gastric openings 14A-14F appear as gaps in the radio-opaque stripe. Radio-opaque stripe 19 serves as a means of determining the location of the catheter in the patient's gastrointestinal tract. The gaps in radio-opaque stripe 19, caused by gastric openings 14A-14F, aid in indicating whether those openings are properly located within the patient's stomach.

The catheter also has a radio-opaque area 20 located at the tube's downstream end 12. Radio-opaque area 20 aids in determining the location of the downstream portion of the catheter within a patient's gastrointestinal tract so that it can be properly positioned in the small intestine.

The catheter of FIG. 1 has a first marking 21, depicted as a single band around the circumference of the tube and a second marking 22, depicted as a double band around the circumference of the tube. First marking 21 and second marking 22 serve as indications of the extent to which the catheter should be inserted when the catheter is used nasally.

Figure 6:
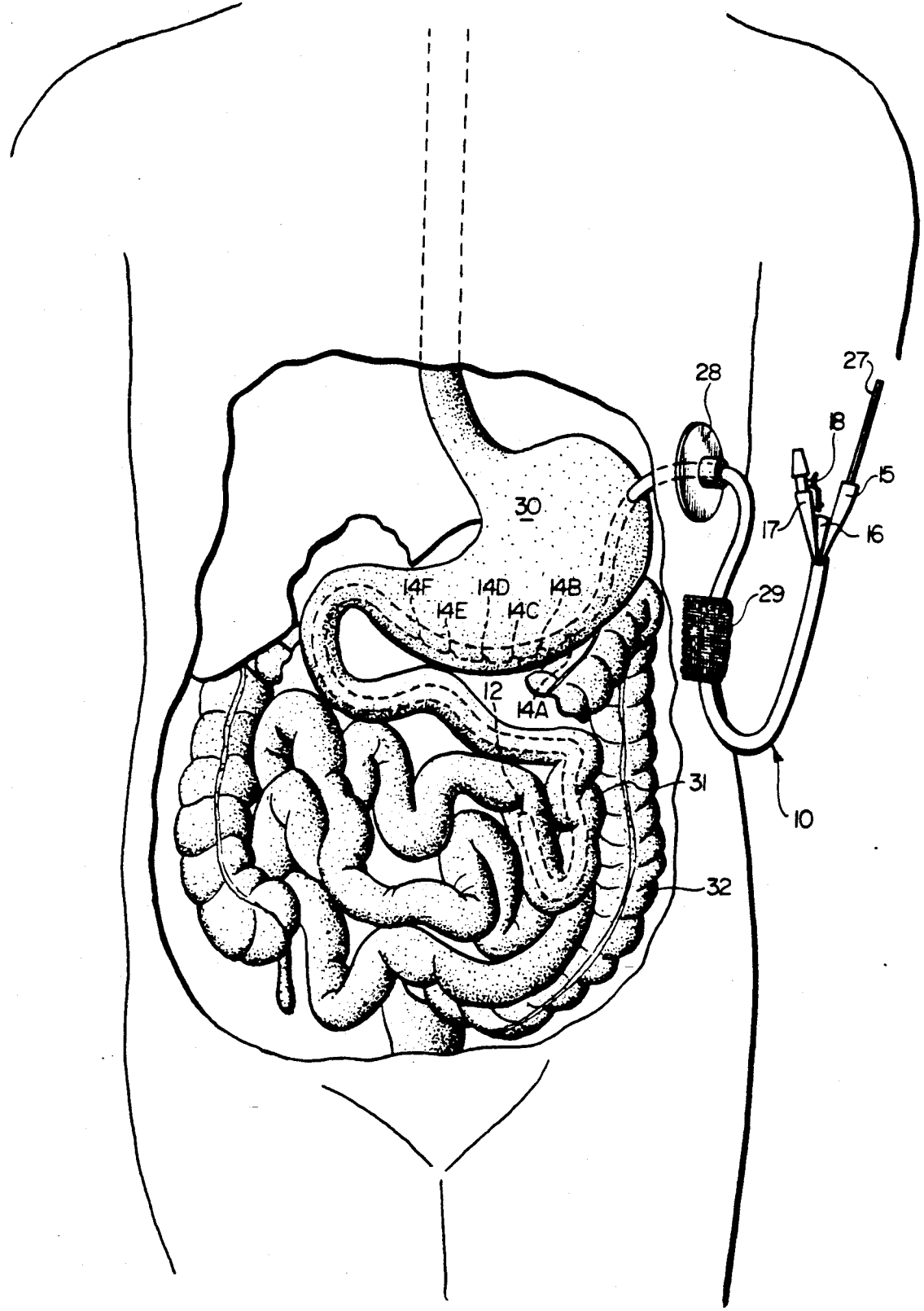
FIG. 6 is a perspective of a human torso, partially cut away, showing a catheter constructed in accordance with the present invention and emplaced within the gastrointestinal tract via a gastrostomy.

FIG. 6 depicts a catheter, constructed in accordance with an embodiment of the present invention, and inserted into a patient's gastrointestinal tract via a gastrostomy incision. The gastrointestinal tract comprises a stomach 30, a small intestine 31 and a large intestine 32. The catheter is positioned so that gastric openings 14A-14F are all located within stomach 30 in order to aspirate the contents of stomach 30. Downstream tube end 12 is located in small intestine 31. The catheter is held in place at the exterior of the patient's body by a tube anchor 28, located at the site of the gastrostomy incision, and by tape 29.

The upstream end portion of guide wire 27 extends out of the catheter through feeding connection fitting 15. Guide wire 27 is used to emplace the catheter into the gastrointestinal tract. The methods of insertion of the catheter using a guide wire are more fully described below.

A catheter used in connection with a gastrostomy preferably has a total length of about 45 inches (114.3 cm). The distance between downstream end 12 and the furthest downstream gastric opening 14F is most preferably about 21 inches (53.3 cm). The distance between adjacent gastric openings in the group 14A-14F is typically about ¾ of an inch (1.9 cm).

FIG. 7 depicts a catheter constructed in accordance with an embodiment of the present invention and inserted nasally into the gastrointestinal tract of a patient. The gastrointestinal tract shown in FIG. 7 comprises an esophagus 34 in addition to stomach 30, small intestine 31 and large intestine 32. The tube has been inserted through a nostril 33 and extends through esophagus 34, through stomach 30 and into small intestine 31. Gastric openings 14A-14F are located within stomach 30. Downstream tube end 12 is located a substantial distance into small intestine 31. The upstream end portion of guide wire 27 extends out of feeding connection fitting 15 at the tube's upstream end 11.

In the embodiment of the invention depicted in FIG. 7, the catheter has a total length of about 60 inches (152.4 cm). The distance from the furthest downstream gastric opening 14F to downstream tube end 12 is about 21 inches (53.3 cm). The distance between adjacent gastric openings is typically about ¾ of an inch (1.9 cm).

In use, when first tube marking 21 is positioned just downstream of nostril 33, second marking 22 will be positioned just upstream of nostril 33. First marking 21 is preferably located about 17½ inches (44.5 cm) upstream of the most upstream gastric opening 14A. Second marking 22 is preferably located about 5 inches (12.7 cm) further upstream of first marking 21. The internal anatomic dimensions of most humans is such that, if a catheter has the dimensions listed above, and the catheter is inserted so that nostril 33 is located between first marking 21 and second marking 22, gastric openings 14A-14F will be located in the patient's stomach.

The catheter can be inserted into the gastrointestinal tract, either nasally or in conjunction with a gastrostomy, using guide wire 27. If a patient already has a catheter emplaced within his gastrointestinal tract, a catheter constructed in accordance with the present invention can easily be used to replace the earlier emplaced catheter. An earlier emplaced catheter might need to be replaced because it does not perform all the functions of the present invention. For instance, if the earlier emplaced catheter merely feeds material into the stomach, it may be desirable to replace that catheter with one which can aspirate the stomach and feed the small intestine. A catheter might also need to be replaced if it has been in use for an extended period of time.

In order to replace a catheter, a guide wire can be inserted into the lumen of a previously emplaced catheter through the open upstream end of that catheter and pushed downstream through the lumen. When the downstream end of the guide wire reaches an open downstream end of the lumen in the previously emplaced catheter, the guide wire is held in place, and the previously emplaced catheter slid over the guide wire and out of the patient's body. In order to slide the earlier emplaced catheter over the guide wire and out of the patient's body, the catheter must, of course, be of a type having an opening at its downstream end much like tip opening 13 of tube 10 in the present invention.

After the earlier catheter has been removed in the manner described in the preceding paragraph, the guide wire will remain emplaced within the gastrointestinal tract to the same extent as the earlier catheter before that catheter was removed. In order to emplace a new catheter, the end of the guide wire extending outside the patient's body, i.e. the upstream end, is inserted through the new catheter's tip opening 13 and into feeding lumen 24. The new catheter is then advanced over the guide wire until the tube's downstream end 12 is at the downstream end of the guide wire, at which time the upstream end of the guide wire should extend out of feeding connection fitting 15.

If the tube's downstream end 12 is now located at a desirable site in the small intestine, the guide wire can be removed through feeding connection fitting 15. If the catheter must be moved further into the gastrointestinal tract, the guide wire should be left in feeding lumen 24. A radiologist can then manipulate the upstream end of the guide wire and catheter, while viewing the catheter and guide wire through a flouroscope, in the manner conventionally used to advance catheters and guide wires through the gastrointestinal tract.

If the catheter is going to be used in the first instance, i.e., when there is no previously emplaced catheter, a guide wire can still be used to emplace the catheter. A guide wire is inserted through feeding connection fitting 15 and into feeding lumen 24. The guide wire is then pushed downstream through feeding lumen 24 until the guide wire's downstream end is within feeding lumen 24 just upstream of the tube's tip opening 13. The catheter and guide wire are then inserted into the patient's body via either a nostril or an opening created by a gastrostomy. The wire and catheter are then manipulated by a radiologist using a flouroscope until the tube's downstream end 12 is at a desired location within the gastrointestinal tract.

It may be desirable to taper the gastrointestinal tube near its downstream end. FIG. 8 shows the tube 10 tapered beginning at taper site 36 near downstream end 12. Tapering the tip insures that the guidewire exits the tube at its most distal extent. This may require a somewhat eccentric tapering of the tip of the tube.

When manipulating a catheter and guide wire through the gastrointestinal tract, it may be desirable to use a tube and/or a guide wire with an angled downstream end portion. FIG. 9 shows tube 10 bent at 35 near downstream end 12. Bend site 35 is located about 2.5 inches (6.5 cm) from downstream end 12 and provides an angle of approximately 30 degrees.

The foregoing detailed description has been given for clearness of understanding only, and no unnecessary limitations should be understood therefrom, as modifications will be obvious to those skilled in the art.

We claim:

1. A catheter for nasogastric insertion into the small intestine, said catheter comprising:
   a flexible tube having upstream and downstream ends;
   said tube having a length such that when the downstream end of the tube is in the small intestine, the upstream end of the tube extends outwardly through the nose;
   said tube having an opening in the tip of the downstream end of the tube;
   a feeding lumen in said tube, communicating with said tip opening in the tube's downstream end and terminating at an upstream end adjacent the upstream end of the tube;
   means at said upstream end of said feeding lumen for connecting said lumen to a source of nutritive or medicinal material;
   said feeding lumen comprising means for receiving a guide wire inserted through the feeding lumen's upstream end or through said tip opening in the downstream end of the tube;
   said tube having gastric openings for aspirating the stomach;
   said tube having a length such that when its downstream end is in the small intestine, at least some of said gastric openings are in the stomach;
   a suction lumen in said tube, communicating with each gastric opening and terminating at an upstream end adjacent the upstream end of the tube;
   means at said upstream end of said suction lumen for connecting said lumen to suction;
   a vent lumen terminating at an upstream end adjacent the upstream end of the tube;

a channel connecting said suction lumen to said vent lumen at a location no further upstream than the furthest downstream gastric opening; and vent means at said upstream end of the vent lumen for communicating said vent lumen to the atmosphere;

said channel, said vent lumen and said vent means comprising means for preventing said gastric openings from becoming clogged when aspirating the stomach.

2. A catheter as recited in claim 1 wherein:

said channel is substantially upstream of said downstream end.

3. A catheter as recited in claim 2 wherein:

said vent lumen and said suction lumen terminate just downstream of said channel.

4. A catheter as recited in claim 1 and comprising:

a radio-opaque stripe on the exterior surface of said tube running from the tube's downstream end to the tube's upstream end.

5. A catheter as recited in claim 4 wherein:

said gastric openings are located on an area of the exterior surface of the tube in line with said radio-opaque stripe; and said gastric openings serve as gaps in said radio-opaque stripe.

6. A catheter as recited in claim 1 and comprising:

a radio-opaque area at the downstream end of said tube.

7. A catheter as recited in claim 1 and comprising:

a first marking on said tube, upstream of said gastric openings; and a second marking on said tube, upstream of said first marking;

the spacings between said gastric openings and said first marking and between said first marking and said second marking being such that when said gastric openings are in a patient's stomach, said first marking is just downstream of the patient's nostril and said second marking is just upstream of the patient's nostril.

8. A catheter as recited in claim 7 wherein:

said first marking is located 17½ inches (44.5 cm) upstream of the most upstream of said gastric openings; and said second marking is located 5 inches (12.7 cm) upstream of said first marking.

9. A catheter as recited in claim 1 wherein:

the distance between the downstream end of the tube and the furthest downstream of said gastric openings is about 21 inches (53.3 cm)

10. A catheter as recited in claim 1 wherein:

said tube has a total length of about 60 inches (152.4 cm).

11. In combination with the catheter recited in claim 1:

a guide wire;

said guide wire comprising means for emplacing said tube within a patient's gastrointestinal tract.

12. A gastrostomy catheter for insertion into the small intestine, said catheter comprising:

a flexible tube having upstream and downstream ends;

said tube having a length such that when the downstream end of the tube is in the small intestine, the upstream end of the tube extends outwardly through the patient's skin adjacent the stomach;

said tube having an opening in the tip of the downstream end of the tube;

a feeding lumen in said tube, communicating with said tip opening in the tube's downstream end and terminating at an upstream end adjacent the upstream end of the tube;

means at said upstream end of said feeding lumen for connecting said lumen to a source of nutritive or medicinal material;

said feeding lumen comprising means for receiving a guide wire inserted through the feeding lumen's upstream end or through said tip opening in the downstream end of the tube;

said tube having gastric openings for aspirating the stomach;

said tube having a length such that when the tube's downstream end is in the small intestine, at least some of said gastric openings are in the stomach;

a suction lumen in said tube, communicating with each gastric opening and terminating at an upstream end adjacent the upstream end of the tube;

means at said upstream end of said suction lumen for connecting said lumen to suction;

a vent lumen terminating at an upstream end adjacent the upstream end of the tube;

a channel connecting said suction lumen to said vent lumen at a location no further upstream than the furthest downstream gastric opening; and vent means at said upstream end of the vent lumen for communicating said vent lumen to the atmosphere;

said channel, said vent lumen and said vent means comprising means for preventing said gastric openings from becoming clogged when aspirating the stomach.

13. A catheter as recited in claims 12 wherein:

said channel is located substantially upstream of said downstream end.

14. A catheter as recited in claim 13 wherein:

said vent lumen and said suction lumen terminate just downstream of said channel.

15. A catheter as recited in claim 12 and comprising:

a radio-opaque stripe on the exterior surface of said tube running from the tube's downstream end to the tube's upstream end.

16. A catheter as recited in claim 15 wherein:

said gastric openings are located on an area of the exterior surface of the tube in line with said radio-opaque stripe;

and said gastric openings serve as gaps in said radio-opaque stripe.

17. The catheter of claim 12 and comprising:

a radio-opaque area at the downstream end of the tube.

18. A catheter as recited in claim 12 wherein:

the distance between the downstream end of the tube and the furthest downstream of said gastric openings is about 21 inches (53.3 cm).

19. A catheter as recited in claim 12 wherein:

said tube has a total length of about 45 inches (114.3 cm).

20. In combination with the catheter recited in claim 12:

a guide wire;

said guide wire comprising means for emplacing said tube within a patient's gastrointestinal tract.

21. The method of inserting an intestinal catheter for aspirating the stomach and feeding the intestines, said catheter having an open upstream end and a downstream end, a tip opening in said downstream end, a feeding lumen communicating with said tip opening and with said open upstream end, gastric openings between said upstream and downstream ends, and a suction lumen connecting each of said gastric openings to said upstream end, said method comprising the steps of:

emplacing a guide wire into the gastrointestinal tract so that one end of said guide wire remains outside the patient's body;

inserting said one end of the guide wire through said tip opening and into said feeding lumen of the catheter;

advancing said catheter over said guide wire and into the patient's gastrointestinal tract;

and removing said guide wire from said catheter through said upstream end of the catheter when the downstream end of the catheter has reached the small intestine.

22. A method as recited in claim 21 wherein:

said guide wire is emplaced within the gastrointestinal tract by inserting said guide wire into the open upstream end of an intestinal catheter also having an open downstream end and which was previously emplaced in the gastrointestinal tract;

said method comprising removing said previously emplaced catheter by withdrawing it over said guide wire and out of the patient's body.

* * * * *